US006933375B2

(12) United States Patent
Falkowski et al.

(10) Patent No.: US 6,933,375 B2
(45) Date of Patent: Aug. 23, 2005

(54) MCFP ENCODING NUCLEIC ACIDS, POLYPEPETIDES, ANTIBODIES AND METHODS OF USE THEREOF

(75) Inventors: Paul Falkowski, Princeton, NJ (US); Yi Sun, New Brunswick, NJ (US); Maxim Gorbunov, Somerset, NJ (US); Kevin Wyman, East Brunswick, NJ (US); Yi-Bu Chen, Highland Park, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 435 days.

(21) Appl. No.: 10/244,779

(22) Filed: Sep. 16, 2002

(65) Prior Publication Data

US 2003/0106078 A1 Jun. 5, 2003

Related U.S. Application Data

(60) Provisional application No. 60/322,189, filed on Sep. 14, 2001.

(51) Int. Cl.[7] .................. C07H 21/04; C12N 15/09; C12N 15/63; C12N 5/00; C07K 14/00
(52) U.S. Cl. .................. 536/23.5; 536/23.1; 435/325; 435/69.1; 435/320.1; 530/350
(58) Field of Search ................. 536/23.5, 23.1; 435/325, 69.1, 320.1; 530/350

(56) References Cited

PUBLICATIONS

NCBI Genbank Record No. AF384683, Montastrea cavernosa green fluorescent protein, published in Genbank on Aug. 27, 2001.*

* cited by examiner

*Primary Examiner*—Robert A. Wax
*Assistant Examiner*—Rosanne Kosson
(74) *Attorney, Agent, or Firm*—Dann, Dorfman, Herrell & Skillman, P.C.

(57) ABSTRACT mcFP encoding nucleic acids, polypeptides and antibodies immunologically specific therefore are disclosed. Methods of use thereof are also provided.

12 Claims, 7 Drawing Sheets

Figure 6

```
GTAATACGACTCACTATAGGGCAAGCAGTGGTATCAACGCAGAGTACGCGGGGATTCACCCT
GGTGATTTGGAAGCGAGCAAATCTAGAAGAACAAGCGCTGTAAGACTGATATCTTACTTTAC
GTCTACCATCATGAGTGTGATTAAATCAGTCATGAAAATCAAGCTGCGTATGGACGGCATTG
TAAACGGGCACAAGTTCATGATTACAGGAGAAGGTGAAGGCAAGCCTTTCGAGGGAACACAC
ACTATAATACTTAAAGTCAAAGAAGGCGGACCTCTGCCTTTCGCTTACGACATCTTGACAAC
AGCATTTCAGTACGGCAACAGGGTATTCACCAAATACCCAAAAGACATACCAGACTATTTCA
AGCAGTCGTTTCCTGAGGGGTATTCCTGGGAAAGAAGCATGACTTTCGAAGACCAGGGCGTT
TGCACCGTCACAAGCGACATAAAGTTGGAAGGCGACTGTTTTTTCTACGAAATTCGATTTTA
TGGTGTGAACTTTCCCTCCAGTGGTCCAGTTATGCAGAAGAAGACGCTGAAATGGGAGCCAT
CCACTGAGAATATGTACGTGCGTGATGGAGTGCTACTGGGGGATGTTAGCAGGACGCTGTTG
CTTGAAGGGGATAAACATCACCGATGTAACTTCAGAAGTACTTACGGGGCAAAGAAGGGTGT
CGTGTTGCCAGAATATCACTTTGTGGACCACCGAATTGAAATTCTGAGCCATGACAAAGATT
ACAACACCGTTGAGGTGTATGAGAATGCCGTTGCTCGCCCTTCTATGCTGCCGGTTAAGGCC
AAGTAAAGGCTTAACTAAAAGCCCAAACGACAACGAGGAGAAAAAAAAAAAAAA
```

Figure 7

```
MSVIKSVMKIKLRMDGIVNGHKFMITGEGEGKPFEGTHTIILKVKEGGPLPFAYDILTTAFQ
YGNRVFTKYPKDIPDYFKQSFPEGYSWERSMTFEDQGVCTVTSDIKLEGDCFFYEIRFYGVN
FPSSGPVMQKKTLKWEPSTENMYVRDGVLLGDVSRTLLLEGDKHHRCNFRSTYGAKKGVVLP
EYHFVDHRIEILSHDKDYNTVEVYENAVARPSMLPVKAK
```

MCFP ENCODING NUCLEIC ACIDS, POLYPEPTIDES, ANTIBODIES AND METHODS OF USE THEREOF

This application claims priority to U.S. Provisional Application No. 60/322,189 filed Sep. 14, 2001, the entire disclosure of which is incorporated by reference herein.

FIELD OF THE INVENTION

This invention relates to the fields of molecular and cellular biology. Specifically, nucleic acids encoding *Montastrea cavernosa* fluorescent protein (mcFP), mcFP polypeptides, mcFP polypeptide-specific antibodies, and methods of use thereof are provided.

BACKGROUND OF THE INVENTION

Several publications are referenced in this application in order to more fully describe the state of the art to which this invention pertains. The disclosure of each of these publications is incorporated by reference herein.

The green fluorescent proteins (GFPs) are a unique class of chromoproteins found in many bioluminescent hydrozoan and anthozoan coelenterates, including the hydromedusan jellyfish (*Aequorea victoria*). The gene for *A. victoria* GFP has been cloned (Prasher et al., 1992, Gene, 111:229–233) and expression of GFP in prokaryotic and eukaryotic hosts results in the synthesis of a functional fluorescent protein with spectral characteristics identical to that of native *A. victoria* GFP (Chalfie et al., 1994, Science, 263:802–805)

GFP is a 238 amino acid protein which has an excitation spectrum characterized by a major excitation peak at 395 nm (blue light), a minor excitation peak at 470 nm, and an emission peak at 509 nm (green light). The GFP absorption bands and emission peak arise from an internal p-hydroxybenzylidene-imidazolidinone chromophore, which is generated by cyclization and oxidation of a Ser-Tyr-Gly (SYG) sequence at residues 65–67 (Cody et al., 1993, Biochemistry 32:1212–1218.

Since fluorescence emission by GFP does not require tissue fixation, exogenous substrates, and/or cofactors, it has become the reporter of choice for studies that require detection of exogenously expressed proteins in living cells and organisms. GFP has been used extensively in a variety of studies to monitor gene expression, cell development, or protein localization (i.e., Chalfie et al., 1994, Science 263:802–805; Heim et al., 1994, Proc. Nat. Acad. Sci. 91:12501–12504; Chalfie and Prasher, WO 95/07463, Mar. 16, 1995). Wild-type GFP has also been used as a tool for visualizing subcellular organelles (Rizzuto et al., 1995, Curr. Biology 5:635–642) and protein transport along a secretory pathway (Kaether and Gerdes, 1995, Febs Letters 369:267–271). The expression of GFP in plant cells (Hu and Cheng, 1995, Febs Letters 369:331–334) and *Drosophila* embryos (Davis et al., 1995, Dev. Biology 170:726–729) has also been described. Such experiments have been performed wherein GFP or a GFP-tagged fusion protein was expressed in a desired cell or cell population, the expression of which was detected by excitation/emission spectra of the exogenous fluorescent protein. It should be noted, however, that GFP and GFP fusion proteins can also be visualized in fixed cells and tissue.

The crystal structures of wild-type GFP and the GFP S65T mutant have been solved and reveal that the GFP tertiary structure resembles a barrel (Ormo et al., 1996, Science 273:1392–1395; Yang, et al., 1996, Nature Biotech 14: 1246–1251). The barrel consists of beta sheets in a compact anti-parallel structure, within which an alpha helix containing the chromophore is contained. As a consequence of this compact structure, GFP is a very stable protein even when exposed to harsh conditions such as protease treatment. The inherent stability of GFP, therefore, renders it an ideal reporter protein in a variety of biological systems. The stability of GFP is, however, problematic in applications requiring detection of rapid or repetitive events.

To expand the utility of GFP to include a broader range of research applications, efforts have been underway to optimize wild-type GFP and identify novel GFP variants to produce GFP reagents. For example, "humanized" GFPs have been generated which are expressed at higher levels in mammalian cells (Haas, et al., 1996, Current Biology 6:315–324; Yang, et al., 1996, Nucl Acids Res 24:4592–4593). Enhanced green fluorescent protein (EGFP) is an example of such a humanized GFP. Mutational screening of GFP DNA sequences has produced mutant GFP DNA sequences which encode GFP variants having different spectral properties, including variants that emit in the blue-, cyan- or yellow-green wavelength.

SUMMARY OF THE INVENTION

This invention provides novel, biological molecules useful for the visualization of protein localization and trafficking in living cells. Such novel, biological molecules can also be used as indicators of ectopic gene expression, thereby providing means to screen and/or select a sub-population of cells or trace cell lineage development. According to one aspect of the invention, isolated nucleic acid molecules encoding a novel fluorescent protein are provided which include sequence encoding said fluorescent protein of between 23 and 28 kilodaltons. A most preferred fluorescent protein of the present invention has a deduced molecular weight of approximately 25,773.43 kilodaltons. The encoded protein, referred to herein as *Montastrea cavernosa* fluorescent protein (hereinafter referred to as mcFP), comprises approximately 225 amino acids. As shown herein, mcFP has an excitation spectrum characterized by a major excitation peak at 434 nm and an emission peak at 477 nm, properties which define mcFP as a cyan (blue) fluorescent protein. In a preferred embodiment of the invention, isolated nucleic acid molecules are provided that encode mcFP. In a particularly preferred embodiment, mcFP has an amino acid sequence the same as SEQ ID NO: 2 (FIG. 7). Exemplary nucleic acid molecules of the invention comprise SEQ ID NO: 1 (FIG. 6) or encode SEQ ID NO: 2 (FIG. 7).

According to another aspect of the present invention, an isolated nucleic acid molecule is provided, which has a sequence selected from the group consisting of: (1) SEQ ID NO: 1; (2) a sequence specifically hybridizing with preselected portions or all of the complementary strand of SEQ ID NO: 1; a sequence encoding preselected portions of SEQ ID NO: 1, (3) a sequence encoding part or all of a polypeptide having amino acid SEQ ID NO: 2. Such partial sequences are useful as probes to identify and isolate homologues of the mcFP gene of the invention. Accordingly, isolated nucleic acid sequences encoding natural allelic variants of SEQ ID NO: 1 are also contemplated to be within the scope of the present invention. The term natural allelic variants will be defined hereinbelow.

mcFP polypeptides may conveniently be obtained by introducing expression vectors into host cells in which the vector is functional, culturing the host cells so that the mcFP polypeptides are produced and recovering the mcFP polypeptides from the host cells or the surrounding medium.

Vectors comprising nucleic acids according to the present invention and host cells comprising such vectors or nucleic acids form further aspects of the present invention.

According to another aspect of the present invention, isolated mcFP protein is provided which has a deduced molecular weight of between 23 and 28 kildaltons. The protein comprises a novel fluorescent protein having spectral properties which distinguish it from pre-existing flourescent proteins, thereby providing reagents for expanding the scope of many biological applications. In a preferred embodiment of the invention, the protein is of coral [*Montastrea cavernosa* (*M. cavernosa*)] origin, and has an amino acid sequence the same as SEQ ID NO: 2. In a further embodiment the protein may be encoded by natural allelic variants of SEQ ID NO: 1. Inasmuch as certain amino acid variations may be present in mcFP protein encoded by natural allelic variants, such proteins are also contemplated to be within the scope of the invention.

According to another aspect of the present invention, antibodies immunologically specific for the proteins described hereinabove are provided.

In yet a further aspect of the invention, methods are provided for generating fusion proteins comprising a nucleotide sequence encoding a desired protein sequence linked in frame to nucleic acids encoding mcFP. Methods are also disclosed for visualizing mcFP-fusion proteins within cells. Methods are also disclosed for visualizing more than one fluorescent fusion protein (e.g., a mcFP-fusion protein and a red fluorescent protein) within a cell by virtue of the inherent and distinct spectral properties of the different fluorescent protein tag moieties.

The nucleic acids, proteins/polypeptides, peptides and antibodies of the present invention may be used to advantage for a variety of applications related to basic and clinical research. The fluorescent protein molecules of the invention may be used as basic research tools to facilitate visualization of protein localization and trafficking in living cells.

In a further aspect of the present invention, there is provided a kit for generating designer recombinant fusion proteins having fluorescent properties, the kit comprising one or more nucleic acid vectors which can be engineered to express a desired fusion protein in cell types suited for expression studies. In a preferred embodiment, the fluorescent properties of a designer recombinant fusion protein are conferred by mcFP, or a portion thereof, which has been appended to a desired protein. Examples of cell types well-suited for expression studies include, but not limited to: bacteria, yeast, insect, and mammalian cells. Other expression systems are also contemplated and are well known to those of skill in the art. The kit will also comprise one or more antibodies capable of specifically binding and/or detecting the fluorescent tag (mcFP component) of mcFP-fusion proteins.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE DRAWINGS

FIG. 6 shows a nucleic acid sequence which encodes full length mcFP (SEQ ID NO: 1).

FIG. 7 shows the amino acid sequence of full length mcFP (SEQ ID NO: 2) encoded by SEQ ID NO: 1.

DETAILED DESCRIPTION OF THE INVENTION

Figure 1:
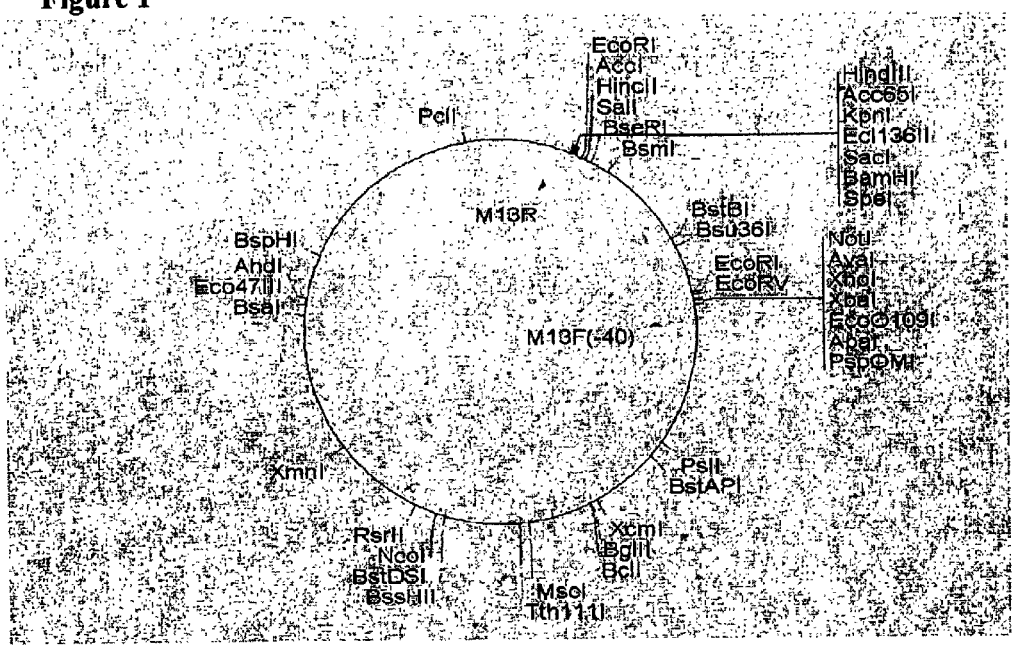
FIG. 1 shows a restriction map of a 3' end of mcFP in the pCRII plasmid (4612 bp)

Despite the great utility of GFP and its derivatives, however, the identification of novel fluorescent proteins with properties that complement GFP would be of use in the art. Novel fluorescent proteins having properties such as different excitation/emission spectra, pH-dependent fluorescence, or a wider temperature range of optimal activity would be of great utility. Novel fluorescent proteins could also be used in applications in which fluorescence resonance energy transfer (FRET) is desirable. The identification of DNA sequences encoding such novel fluorescent proteins would, therefore, address a deficiency in the prior art by providing promising tools of utility for basic research and clinical applications. The present invention fulfills this long-standing need in the art.

Since fluorescence emission by mcFP does not require tissue fixation, exogenous substrates, and/or cofactors, it is an ideal reporter for studies that require detection of exogenously expressed proteins in living cells and organisms. mcFP can be expressed or introduced into living cells either alone or as a component of a fusion protein. mcFP can be used in studies designed to monitor gene expression, cell development, or protein localization utilizing protocols to track fluorescent proteins. Such protocols are well known to those of skill in the art (i.e., Chalfie et al., 1994, Science 263:802–805; Heim et al., 1994, Proc. Nat. Acad. Sci. 91:12501–12504; Chalfie and Prasher, WO 95/07463, Mar. 16, 1995). mcFP can also be utilized as a tool for visualizing subcellular organelles (Rizzuto et al., 1995, Curr. Biology 5:635–642) and protein transport along intracellular secretory pathways (Kaether and Gerdes, 1995, Febs Letters 369:267–271). mcFP expression can also be used to track plant cells or cells in Drosophila embryos as previously described (Hu and Cheng, 1995, Febs Lett 369:331–334; Leffel et al., 1997, Biotechniques 23:912–918; Gerdes and Kaether, 1996, FEBS Lett 389:44–47; Davis et al., 1995, Dev. Biology 170:726–729). In such experiments, mcFP or a mcFP-tagged fusion protein can be expressed in a desired cell or cell population and detected by virtue of the excitation/emission spectra of the exogenous fluorescent protein. Notably, there are some experimental applications which preclude use of GFP due to the range of its emission spectra and for which mcFP is ideally suited due to its distinct emission spectra (see below; Lukyanoy et al., WO 00/34326).

It will be apparent to those of skill in the art that mcFP, or a variant or fragment thereof, can be used either alone or in conjunction with other fluorescent protein(s) having distinct excitation/emission spectra for many of the experimental applications envisioned.

The identification of novel fluorescent proteins, such as mcFP, which have distinct excitation/emission spectra greatly expands the applications for which fluorescent proteins can be used. mcFP or a mcFP-tagged fusion protein can be expressed in conjunction with at least one other fluorescent protein, such as GFP, to facilitate the visualization of two or more proteins within living cells. The ability to perform such co-localization studies in living cells provides researchers and clinicians with invaluable tools for deciphering complicated networks of protein interactions and cellular response to therapeutic agents.

The ability to detect at least one fluorescent protein (i.e., mcFP) within living cells that are either maintained in culture ex vivo or found within an intact organism makes these reagents ideally suited to studies requiring real-time analysis of biological processes. Utilizing methods known to those of skill in the art, mcFP can be used as a tag or label with which to track a specific protein, so as to examine the subcellular localization and dynamics of the protein (see Chalfie, 1995, Photochem Photobiol 62:651–656; Cubitt et al., 1995, Trends Biochem Sci 20:448–455; Misteli et al., 1997, Nat Biotechno 15:961–964; Baumann and Reyes, 1999, Methods 19:353–361). mcFP can also be used in time-lapse microscopy studies to monitor cytoskeletal or organelle movements within a cell; for such applications, mcFP can be used as a tag to track a specific component (i.e., protein) of these or other cellular structures as described previously (see Sullivan and Shelby, 1999, Methods Cell Biol 58:183–202; Chang, 2000, Microsci Res Tech 49:161–167).

mcFP or a mcFP-fusion protein can also be used in real-time and time-lapse laser confocal microscopy to observe cell shape changes and tissue movements in living, unperturbed embryos and animals. For example, mcFP or a mcFP-fusion protein can be used to examine cell shape changes and movement during morphogenesis and wound healing as described by Kiehart et al. (2000, J Cell Biol 149:471–490). This study established the Drosophila embryo as a model system for molecular characterization of the cellular events associated with wound healing (Kiehart et al., 2000, J Cell Biol 149:471–490). It is evident that such applications provide the means to determine the modulating roles of chemical therapeutic compounds in regulating such clinically relevant cellular processes. For example, expression of mcFP or a mcFP-fusion protein in Drosophila epidermal cells can be used as means to visualize the effect of a battery of chemical compounds on wound healing in this model system. Such chemical compounds can be tested individually or in cocktails containing at least one chemical compound. Such a simple and cost effective screening system provides means to screen a large number of chemical compounds to ascertain their value as potential therapeutic agents. Therapeutic agents identified in such a model system can then be tested in mammalian model systems to determine if they promote wound healing in other animal species. Therapeutic agents so identified, which are deemed safe in humans, can ultimately be tested for the ability to promote wound healing in human patients.

In another embodiment of the invention, mcFP, a mcFP-fusion protein, or mutants thereof can be used as dynamic markers of intracellular signaling events, such as those events characterized by fluctuations in the level of second messengers [i.e., $Ca^{2+}$ or cyclic adenosine monophosphate (cAMP)]. Moreover, mcFP, a mcFP-fusion protein, or mutants thereof can also be used as probes to detect pH changes in specific cell compartments. Techniques for the above applications have been previously described (Zaccolo and Pozzan, 2000, IUBMB Life 49:375–379). In another embodiment of the invention, mcFP or a mcFP-fusion protein can be utilized in studies which assess the correlation of protein dynamics with changes in protein structure or ligand binding. Techniques describing such an application have been described (Chamberlain and Hahn, 2000, Traffic 1:755–762) and make use of fluorescence resonance energy transfer (FRET), site-specific protein labeling chemistry, and dyes that indicate structural changes in their proximity.

In another embodiment of the invention, expression of mcFP or a mcFP-fusion protein can be used in digital imaging microscopy, an enhanced form of epifluorescence microscopy, which can be used to produce high resolution three-dimensional images of samples labeled with fluorescent proteins. Methods describing such techniques have been described (Rizzuto et al., 1998, Trends Cell Biol 8:288–292; Haseloff, 1999, Methods Cell Biol 58:139–151).

In another embodiment of the invention, expression of mcFP or a mcFP-fusion protein can be used as means to improve the efficiency of transgenic livestock production. The efficient production of transgenic animals is an important goal for basic scientific research as well as the pharmaceutical industry. Genetically engineered farm animals are routinely utilized as model systems of human disease and in production of proteins generated for use in human therapy. Methods describing the utility of screening for GFP expression as a means to indicate successful gene integration have been described (Takada and Tsujimoto, 1998, Nippon Yakurigaku Zasshi 111:357–362).

In another embodiment of the invention, expression of mcFP or a mcFP-fusion protein can be used to reveal cellular and molecular changes associated with cancer that occur in intact living animal models of human disease. The low level transmission of light through mammalian tissue facilitates detection of the targeted expression of fluorescent or bioluminescent proteins in tumors using sensitive photon detection systems. Targeted expression of mcFP or a mcFP-fusion protein, as visualized by sensitive photon detection systems, can be used to reveal the molecular and cellular features of neoplasia in vivo. Techniques describing the methods of such an application have been described (Contag et al., 2000, Neoplasia 2:41–52). Utilization of such methods facilitates a non-invasive assessment of tumor growth and regression in experimental animals treated with various therapeutic agents. Such real time spatiotemporal analysis of tumor cell growth elucidates the dynamic nature of neoplastic disease and enables the rapid assessment and optimization of effective treatment regimens. Moreover, such methods can be used to predict the utility of an animal model system for a human neoplastic disease and advance the development of effective therapeutic strategies for the treatment of human patients (Contag et al., 2000, Neoplasia 2:41–52).

In another embodiment of the invention, expression of mcFP or a mcFP-fusion protein can be used to improve the efficiency of techniques related to human gene therapy. The readily detectable expression of mcFP or a mcFP-fusion protein can be used as means to screen for successful gene transfer and select for transduced cells via fluorescence activated sorting (FACS-sorting). Pure populations of transduced cells, which express both mcFP and a transgene that can complement a human disorder, for example, can then be used in transfer experiments. The efficiency of gene therapy is greatly enhanced following transfer of pure populations of transduced cells. Methods describing these techniques have been described (Pawliuk et al., 1998, Ann NY Acad Sci 850:151–162). One of skill in the art would appreciate that expression of mcFP or a mcFP-fusion protein can also be used to track transduced cells over time to assess the viability, localization, and differentiation of these cells in situ.

In another embodiment of the invention, expression of mcFP or a mcFP-fusion protein can be used for a variety of applications in plants. Techniques delineating such applications have been described (Leffel et al., 1997, Biotechniques 23:912–918). For example, expression mcFP or a mcFP-fusion protein can be used as means to monitor transgene movement and transgenic animals in the field.

In another embodiment of the invention, expression of mcFP or a mcFP-fusion protein can be used in the technique of surgical orthotopic implantation (SOI), which involves the transplantation of histologically-intact fragments of human cancer tissue into the corresponding organ of immunodeficient rodents (Hoffman, 1999, Invest New Drugs 17:343–359). Utilizing the SOI method, a cancer cell line or a tumor explant can be engineered to express mcFP or a mcFP-fusion protein so as to facilitate visualization of metastasizing cells in fresh tissue at ultra-high resolution and externally image metastases. SOI models for a number human cancers have been developed, including spontaneous bone metastatic models of prostate cancer, breast cancer and lung cancer; a spontaneous liver and lymph node ultra-metastatic model of colon cancer; and metastatic models of pancreatic, stomach, ovarian, bladder, and kidney cancer. A skilled artisan would appreciate that such model systems provide means to screen for therapeutic agents of utility in the treatment of cancer patients. As such, SOI models are ideal for innovative drug discovery and mechanism studies and thus serve as an interface for pre-clinical and clinical research related to drug development (Hoffman, 1999, Invest New Drugs 17:343–359). The use of GFP for similar applications has been previously described, see for example U.S. Pat. No. 6,251,384 the entire disclosure of which is incorporated herein by reference.

In another embodiment of the invention, expression of mcFP or a mcFP-fusion protein can be used in conjunction with high throughput screening (HTS) methods developed to facilitate the discovery of new drugs. Luminescence-based assays are preferable to radiolabel-based assays in HTS applications since they provide an ideal combination of sensitivity, ease of operation, and cost effectiveness, and are thus well suited to miniaturization. HTS applications describing methods for utilization of at least one fluorescent protein, for example mcFP or a mcFP-fusion protein, have been described (Deo and Daunert, 2001, Fresenius J Anal Chem 369:258–266).

In another embodiment of the invention, expression of mcFP or a mcFP-fusion protein can be used in a variety of gene therapy techniques. For example, a mcFP-tagged therapeutic protein can be constructed which, by virtue of the mcFP-tag, can be visualized to assess the expression level and spatiotemporal expression pattern of a therapeutic gene. The ability to measure such parameters provides information which is essential to establish correlations between gene transfer rate and therapeutic outcome.

In another embodiment of the invention, expression of mcFP or a mcFP-fusion protein can be used to study processes related to blood circulation and cell trafficking. Since blood absorbs green fluorescence, GFP is not a useful tool for such applications. mcFP or a mcFP-fusion protein, however, are ideally suited for such applications because the major wavelength of mcFP emission is 477 nm, which can be visualized in blood. Expression of mcFP or a mcFP-fusion protein in a population of circulating cells, therefore, facilitates tracking of these cells in the blood. In such an application, mcFP or a mcFP-fusion protein could be used either alone, or in conjunction with a different fluorescent protein having distinct spectral properties. The simultaneous detection of two distinct fluorescent proteins, either in circulating blood or in cell populations isolated from blood, could be useful in the reduction of background fluorescence problems associated with some tissue and cell types (Lukyanoy et al., WO 00/34326). A skilled artisan would appreciate that such applications could be used to track a specific cell population and/or assess the efficacy of a therapeutic agent that impacts a specific cell population.

In another embodiment of the invention, expression of mcFP or a mcFP-fusion protein can be used in conjunction with laser microsurgery to ablate a cellular component or tissue whose boundaries can be defined by light microscopy. Cellular components which can be targeted utilizing this approach include, for example: chromosomes, spindle fibers, bundles of keratin or actin filaments, mitochondria, and vacuoles. The definition of poorly resolved intracellular components or tissue can be enhanced for selective destruction by tagging one or more proteins that localize to the desired target with mcFP. The localization of mcFP to a target clearly defines the target region, which can consequently be destroyed by a focused stream of green laser light. The application of such techniques has been previously described (Khodjakov et al., 1997, Cell Motil Cytoskeleton 38:311–317). A skilled artisan would appreciate that such techniques, in combination with surgery, can be applied to the targeted destruction of a specific cell type in an intact animal or human patient for the purpose of therapeutic intervention. In a particular embodiment of the invention, such a combined technique can be used to ablate tumor cells in situ in a human or animal patient.

In another embodiment of the invention, expression of mcFP or a mcFP-fusion protein can be used in applications that utilize FRET to monitor protein-protein interactions. This technique involves utilization of two fluorescent proteins, each of which has a distinct excitation/emission spectra. In such an application, mcFP or a mcFP-fusion protein can be fused via a linker to a spectrally distinct fluorescent protein (i.e., GFP). As revealed following excitation, such fluorescent fusion proteins can exhibit spectral properties indicating that energy transfer is occurring between the two spectrally distinct components. Upon cleavage of the linker, the two fluorescent proteins dissociate, as registered by a decrease in energy transfer. Such applications underscore the feasibility of utilizing FRET between mcFP and a spectrally distinct second fluorescent protein to monitor protein-protein interactions, facilitate high-throughput drug screens directed toward modulating protein-protein interactions, and enable intracellular screens for modulators of protein function (i.e., protease inhibitors). Such techniques have been described (Mitra et al., 1996, 173:13–17).

In another embodiment of the invention, expression of mcFP or a mcFP-fusion protein can be used as indicators of physiological condition, biosensors, and reagents conferring photochemical memory. Such techniques have been previously described (Tsein, 1998, Annu Rev Biochem 67:509–544).

I. Definitions:

Various terms relating to the biological molecules of the present invention are used hereinabove and also throughout the specifications and claims.

As used herein, the term "GFP" refers to the basic green fluorescent protein from *Aequorea Victoria*, including prior art versions of GFP engineered to provide greater fluorescence or fluoresce at different wavelengths. The sequence of *Aequorea Victoria* GFP has been disclosed previously (Prasher et al. (1992, Gene 111:229–33).

As used herein, the term "EGFP" refers to a mutant variant of GFP having two amino acid substitutions: F64L and S65T (Heim et al., 1995, Nature 373:663–664). The term "humanized" refers to changes made to the GFP nucleic acid sequence to optimize codon usage for expression of the protein in human cells (Yang et al., 1996, Nucleic Acids Research 24:4592–4593).

As used herein, the term "benthic organism" refers to organisms that live in, on, or near the bottom of salt and fresh waters, including plants, invertebrates, and fish of all sizes. Corals are benthic organisms which are tiny animals that are generally grouped together by the thousands, forming colonies that attach to hard surfaces of the sea floor. The following is a list of some exemplary organisms relevant to the present invention: *Montastrea cavernosa, M. faveolata, M. annularis, Diploria labiriathisformis, Colpophyllia natans, Mannicina areolata, Mycetonphylla* sp., *Porites astreoides, Scolymia cubensis, S. wellsi, Meandrina meandrites, Leptoseris cucullata, Favia fragum, Eusmilia fastigiata, Agaricia fragilis, Mycetonphyllia lamarckiana.*

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "promoter region" refers to the transcriptional regulatory regions of a gene, which may be found at the 5' or 3' side of the coding region, or within the coding region, or within introns.

The term "vector" refers to a small carrier DNA molecule into which a DNA sequence can be inserted for introduction into a host cell where it will be replicated. An "expression vector" is a specialized vector that contains a gene with the necessary regulatory regions needed for expression in a host cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

The phrase "consisting essentially of" when referring to a particular nucleotide or amino acid means a sequence having the properties of a given SEQ ID No:. For example, when used in reference to an amino acid sequence, the phrase includes the sequence per se and molecular modifications that would not affect the basic and novel characteristics of the sequence.

With respect to antibodies of the invention, the term "immunologically specific" refers to antibodies that bind to one or more epitopes of a protein of interest (e.g., mcFP protein), but which do not substantially recognize and bind other molecules in a sample containing a mixed population of antigenic biological molecules.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15–25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield an primer extension product. The primer may vary in length depending on the particular conditions and requirement of the application. For example, in diagnostic applications, the oligonucleotide primer is typically 15–25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "percent identical" is used herein with reference to comparisons among nucleic acid or amino acid sequences. Nucleic acid and amino acid sequences are often compared using computer programs that align sequences of nucleic or amino acids thus defining the differences between the two. For purposes of this invention comparisons of nucleic acid sequences are performed using the GCG Wisconsin Package version 9.1, available from the Genetics Computer Group in Madison, Wis. For convenience, the default parameters (gap creation penalty=12, gap extension penalty=4) specified by that program are intended for use herein to compare sequence identity. Alternately, the Blastn 2.0 program provided by the National Center for Biotechnology Information (at http://www.ncbi.nlm.nih.gov/blast/; Altschul et al., 1990, J Mol Biol 215:403–410) using a gapped alignment with default parameters, may be used to determine the level of identity and similarity between nucleic acid sequences and amino acid sequences.

The present invention also includes active portions, fragments, and derivatives of the mcFP polypeptide of the invention. An "active portion" of a mcFP protein polypeptide means a peptide which is less than said full length mcFP protein polypeptide, but which retains its essential biological activity, e.g., fluorescence following excitation at a specific wavelength.

An exemplary active portion, fragment, or derivative of mcFP is a chromophore domain which comprises the essential Q, Y, and G residues (amino acids 62–64) of full length mcFP. A chromophore domain comprising these essential residues (or chromophore core) may also include ten or more amino acid sequences which flank the chromophore core on either side in mcFP (i.e., amino acids 52–74).

A "fragment" of mcFP fluorescent protein polypeptide means a stretch of amino acid residues of at least about five to seven contiguous amino acids, often at least about seven to nine contiguous amino acids, typically at least about nine to thirteen contiguous amino acids and, most preferably, at least about twenty to thirty or more contiguous amino acids. Fragments of mcFP polypeptide sequence, antigenic determinants, or epitopes are useful for raising antibodies to a portion of said mcFP protein amino acid sequence.

A "derivative" of mcFP polypeptide or a fragment thereof means a polypeptide modified by varying the amino acid sequence of the protein, e.g. by manipulation of the nucleic acid encoding the protein or by altering the protein itself. Such derivatives of the natural amino acid sequence may involve insertion, addition, deletion or substitution of one or more amino acids, without fundamentally altering the essential activity of the wildtype mcFP protein polypeptide.

As mentioned above, the mcFP polypeptide or protein of the invention includes any analogue, fragment, derivative or mutant which is derived from mcFP and which retains at least one property or other characteristic of mcFP. Different "variants" of mcFP exist in nature. These variants may be alleles characterized by differences in the nucleotide sequences of the gene coding for the protein, or may involve different RNA processing or post-translational modifications. The skilled person can produce variants having single or multiple amino acid substitutions, deletions, additions or replacements. These variants may include inter alia: (a) variants in which one or more amino acids residues are substituted with conservative or non-conservative amino acids, (b) variants in which one or more amino acids are added to the mcFP, (c) variants in which one or more amino acids include a substituent group, and (d) variants in which mcFP is fused with another peptide or polypeptide such as a fusion partner, a protein tag or other chemical moiety, that may confer useful properties to mcFP, such as, for example, an epitope for an antibody, a polyhistidine sequence, a biotin moiety and the like. Other mcFP-like proteins of the invention include variants in which amino acid residues from one species are substituted for the corresponding residue in another species, either at the conserved or non-conserved positions. In another embodiment, amino acid residues at non-conserved positions are substituted with conservative or non-conservative residues. The techniques for obtaining these variants, including genetic (suppressions, deletions, mutations, etc.), chemical, and enzymatic techniques are known to the person having ordinary skill in the art.

To the extent such allelic variations, analogues, fragments, derivatives, mutants, and modifications, including alternative nucleic acid processing forms and alternative post-translational modification forms result in derivatives of mcFP that retain any of the biological properties of mcFP, they are included within the scope of this invention.

The term "functional" as used herein implies that the nucleic or amino acid sequence is functional for the recited assay or purpose.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples and they do not need to be listed here. Further, the term "specific binding pair" is also applicable where either or both of the specific binding member and the binding partner comprise a part of a large molecule. In embodiments in which the specific binding pair are nucleic acid sequences, they will be of a length to hybridize to each other under conditions of the assay, preferably greater than 10 nucleotides long, more preferably greater than 15 or 20 nucleotides long.

II. Preparation of mcFP-Encoding Nucleic Acid Molecules; mcFP Polypeptides, and Antibodies Thereto

A. Nucleic Acid Molecules

Nucleic acid molecules encoding the fluorescent protein mcFP of the invention may be prepared by two general methods: (1) Synthesis from appropriate nucleotide triphosphates, or (2) Isolation from biological sources. Both methods utilize protocols well known in the art.

The availability of nucleotide sequence information, such as a full length nucleic acid sequence having SEQ ID NO: 1, enables preparation of isolated nucleic acid molecules of the invention by oligonucleotide synthesis. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a 1.4 kb double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire 1.4 kb double-stranded molecule. A synthetic DNA molecule so constructed may then be cloned and amplified in an appropriate vector.

Nucleic acid sequences encoding mcFP may be isolated from appropriate biological sources using methods known in the art. In a preferred embodiment, a cDNA clone is isolated from a cDNA expression library of *M. cavernosa* origin. In an alternative embodiment, utilizing the sequence information provided by the cDNA sequence corresponding to a mcFP, a genomic clone encoding mcFP protein may be isolated. Alternatively, cDNA or genomic clones having homology mcFP protein may be isolated from other species, such as other organisms which can emit fluorescence, using oligonucleotide probes corresponding to predetermined sequences within the mcFP gene.

In accordance with the present invention, nucleic acids having the appropriate level of sequence homology with the protein coding region of SEQ ID NO: 1 may be identified by using hybridization and washing conditions of appropriate stringency. For example, hybridizations may be performed, according to the method of Sambrook et al., (supra) using a hybridization solution comprising: 5×SSC, 5× Denhardt's reagent, 0.5–1.0% SDS, 100 µg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 0.5–1% SDS; (2) 15 minutes at room temperature in 2×SSC and 0.1% SDS; (3) 30 minutes-1 hour at 37° C. in 1×SSC and 1% SDS; (4) 2 hours at 42–65° C. in 1×SSC and 1% SDS, changing the solution every 30 minutes.

One common formula for calculating the stringency conditions required to achieve hybridization between nucleic acid molecules of a specified sequence homology is (Sambrook et al., 1989):

$$T_m = 81.5° C. + 16.6 \text{Log}[Na^+] + 0.41(\% \ G+C) - 0.63 \ (\% \ \text{formamide}) - 600/\#bp \ \text{in duplex}$$

As an illustration of the above formula, using [Na+]= [0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

Nucleic acids of the present invention may be maintained as DNA in any convenient cloning vector. In a preferred embodiment, clones are maintained in a plasmid cloning/ expression vector, such as pBluescript (Stratagene, La Jolla, Calif.), which is propagated in a suitable *E. coli* host cell. Genomic clones of the invention encoding the *M. cavernosa* mcFP polypeptide gene may be maintained in lambda phage FIX II (Stratagene).

mcFP polypeptide-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the cDNA having SEQ ID NO: 1. Such oligonucleotides are useful as probes for detecting or isolating mcFP protein genes.

It will be appreciated by persons skilled in the art that variants (e.g., allelic variants) of these sequences may exist in a population of a species having fluorescent proteins (such as, but not limited to, different coral species as described herein) must be taken into account when designing and/or utilizing oligonucleotides of the invention. Accordingly, it is within the scope of the present invention to encompass such variants, with respect to the mcFP protein sequence disclosed herein or the oligonucleotides targeted to specific locations on the respective gene or RNA transcript. With respect to the inclusion of such variants, the term "natural allelic variants" is used herein to refer to various specific nucleotide sequences and variants thereof that would occur in, for example, *M. cavernosa*. Genetic polymorphisms giving rise to conservative or neutral amino acid substitutions in the encoded protein are examples of such variants.

"Natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 75%, but often, more than 90%, of the nucleotides of the sequence match over the defined length of the nucleic acid sequence referred to using a specific SEQ ID NO. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

Additionally, the term "substantially complementary" refers to oligo sequences that may not be perfectly matched to a target sequence, but the mismatches do not materially affect the ability of the oligo to hybridize with its target sequence under the conditions described.

Thus, the coding sequence may be that shown in SEQ ID NO: 1 or it may be a mutant, variant, derivative or allele of this sequence. The sequence may differ from that shown by a change which is one or more of addition, insertion, deletion and substitution of one or more nucleotides of the sequence shown. Changes to a nucleotide sequence may result in an amino acid change at the protein level, or not, as determined by the genetic code.

Thus, nucleic acid according to the present invention may include a sequence different from the sequence shown in SEQ ID NO: 1 yet encode a polypeptide with the same amino acid sequence.

On the other hand, the encoded polypeptide may comprise an amino acid sequence which differs by one or more amino acid residues from the amino acid sequence shown in SEQ ID NO: 2. Nucleic acid encoding a polypeptide which is an amino acid sequence mutant, variant, derivative or allele of the sequence shown in SEQ ID NO: 1 is further provided by the present invention. Nucleic acid encoding such a polypeptide may show greater than 60% homology with the coding sequence shown in SEQ ID NO: 1, greater than about 70% homology, greater than about 80% homology, greater than about 90% homology or greater than about 95% homology.

The present invention provides a method of obtaining nucleic acid of interest, the method including hybridization of a probe having part or all of the sequence shown in SEQ ID NO: 1, or a complementary sequence, to target nucleic acid. Hybridization is generally followed by identification of successful hybridization and isolation of nucleic acid which has hybridized to the probe, which may involve one or more steps of PCR.

Such oligonucleotide probes or primers, as well as the full-length sequence (and mutants, alleles, variants, and derivatives) are useful for identifying variants of mcFP having novel properties such as a unique excitation/emission spectra and/or enhanced longevity of the mcFP fluorescent signal. The conditions of the hybridization can be controlled to minimize non-specific binding, and preferably stringent to moderately stringent hybridization conditions are used. The skilled person is readily able to design such probes, label them and devise suitable conditions for hybridization reactions, assisted by textbooks such as Sambrook et al (1989) and Ausubel et al (1992).

In some preferred embodiments, oligonucleotides according to the present invention that are fragments of the sequence shown in SEQ ID NO: 1 or any allele associated with an ability to emit fluorescence, are at least about 10 nucleotides in length, more preferably at least 15 nucleotides in length, more preferably at least about 20 nucleotides in length. Such fragments themselves individually represent aspects of the present invention. Fragments and other oligonucleotides may be used as primers or probes as discussed but may also be generated (e.g. by PCR) in methods concerned with determining the presence in a test sample of a sequence indicative of cancer susceptibility.

B. Proteins mcFP is a novel fluorescent protein having properties which confer advantages in a variety of scientific applications, including features relating to spectral properties such as wavelengths of maximal excitation/emission and duration time of fluorescence emission that differ from those of known fluorescent proteins. Full-length mcFP polypeptide of the present invention may be prepared in a variety of ways, according to known methods. The protein may be purified from appropriate sources, e.g., transformed bacterial or animal cultured cells or tissues derived from organisms containing mcFP protein (including, but not restricted to *M. cavernosa*), by immunoaffinity purification. However, this is not a preferred method due to the low amount of protein likely to be present in a given cell type at any time. The availability of nucleic acid molecules encoding mcFP polypeptide enables production of mcFP protein using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or BRL, Rockville, Md.

Alternatively, according to a preferred embodiment, larger quantities of mcFP may be produced by expression in a suitable prokaryotic or eukaryotic system. For example, part or all of a DNA molecule, such as a nucleic acid sequence having SEQ ID NO: 1 may be inserted into a plasmid vector adapted for expression in a bacterial cell, such as *E. coli*. Alternatively, in a preferred embodiment, fluorescently tagged fusion proteins comprising mcFP linked to a desired polypeptide can be generated. Such mcFP-tagged fusion proteins are encoded by part or all of a DNA molecule, such as the nucleic acid sequence having SEQ ID NO: 1, ligated in the correct codon frame to a nucleotide sequence encoding a portion or all of a desired polypeptide which is inserted into a plasmid vector adapted for expression in a bacterial cell, such as *E. coli* or a eukaryotic cell, such as, but limited to, yeast and mammalian cells. Vectors such as those described above comprise the regulatory elements necessary for expression of the DNA in the host cell (e.g. *E. coli*) positioned in such a manner as to permit expression of the DNA in the host cell. Such regulatory elements required for expression include promoter sequences, transcription initiation sequences and, optionally, enhancer sequences.

mcFP, or fusion proteins thereof, produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6–8 histidine residues at their N-terminus or C-terminus. Alternative tags may comprise the FLAG epitope, GST or the hemagglutinin epitope. Such methods are commonly used by skilled practitioners.

mcFP, and fusion proteins thereof, of the invention, prepared by the aforementioned methods, may be analyzed according to standard procedures. For example, such proteins may be subjected to amino acid sequence analysis, according to known methods.

As discussed above, a convenient way of producing a polypeptide according to the present invention is to express nucleic acid encoding it, by use of the nucleic acid in an expression system. The use of expression systems has reached an advanced degree of sophistication today.

Accordingly, the present invention also encompasses a method of making a polypeptide (as disclosed), the method including expression from nucleic acid encoding the polypeptide (generally nucleic acid according to the invention). This may conveniently be achieved by growing a host cell in culture, containing such a vector, under appropriate conditions which cause or allow production of the polypeptide. Polypeptides may also be produced in in vitro systems, such as reticulocyte lysate.

Polypeptides which are amino acid sequence variants, alleles, derivatives or mutants are also provided by the present invention. A polypeptide which is a variant, allele, derivative, or mutant may have an amino acid sequence that differs from that given in SEQ ID NO: 2 by one or more of addition, substitution, deletion and insertion of one or more amino acids. Preferred such polypeptides exhibit fluorescence, immunological cross-reactivity with an antibody reactive with the polypeptide for the sequence given in SEQ ID NO: 2, or share an epitope with the polypeptide for which sequence is given in SEQ ID NO: 2 (as determined for example by immunological cross-reactivity between the two polypeptides).

A polypeptide which is an amino acid sequence variant, allele, derivative or mutant of the amino acid sequence shown in SEQ ID NO: 2 may comprise an amino acid sequence which shares greater than about 35% sequence identity with the sequence shown, greater than about 40%, greater than about 50%, greater than about 60%, greater than about 70%, greater than about 80%, greater than about 90% or greater than about 95%. Particular amino acid sequence variants may differ from that shown in SEQ ID NO: 2 by insertion, addition, substition or deletion of 1 amino acid, 2, 3, 4, 5–10, 10–20, 20–30, 30–40, 40–50, 50–100, 100–150, or more than 150 amino acids.

The present invention also provides antibodies capable of immunospecifically binding to proteins of the invention. Polyclonal antibodies directed toward mcFP may be prepared according to standard methods. In a preferred embodiment, monoclonal antibodies are prepared, which react immunospecifically with various epitopes of mcFP. Monoclonal antibodies may be prepared according to general methods of Köhler and Milstein, following standard protocols. Polyclonal or monoclonal antibodies that immunospecifically interact with mcFP can be utilized for identifying and purifying mcFP protein. For example, antibodies may be utilized for affinity separation of proteins with which they immunospecifically interact. Antibodies may also be used to immunoprecipitate proteins from a sample containing a mixture of proteins and other biological molecules. Other uses of anti-mcFP polypeptide antibodies are described below.

Antibodies according to the present invention may be modified in a number of ways. Indeed the term "antibody" should be construed as covering any binding substance having a binding domain with the required specificity. Thus, the invention covers antibody fragments, derivatives, functional equivalents and homologues of antibodies, including synthetic molecules and molecules whose shape mimics that of an antibody enabling it to bind an antigen or epitope.

Exemplary antibody fragments, capable of binding an antigen or other binding partner, are Fab fragment consisting of the VL, VH, C1 and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

III. Uses of mcFP Polypeptide-Encoding Nucleic Acids, Protein and Antibodies Thereto mcFP nucleic acids, protein and antibodies thereto, according to this invention, may be used, for example, as research tools to detect the expression of specific proteins in living cells, localize proteins to specific cellular compartments, screen and select for transformed/transfected cells, track cell lineage in the course of development, and visualize protein-protein interactions in living cells.

A. mcFP-Encoding Nucleic Acids mcFP polypeptide-encoding nucleic acids may be used for a variety of purposes in accordance with the present invention. mcFP polypeptide-encoding DNA, RNA, or fragments thereof may be used as probes to detect the presence of and/or expression of genes encoding mcFP-like fluorescent proteins in different species and define tissue specific expression patterns in such a species. Such fluorescent properties may exhibit useful properties such as, but not limited to, unique spectral properties. Methods in which mcFP polypeptide-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR).

The mcFP polypeptide-encoding nucleic acids of the invention may also be utilized as probes to identify related genes from other species (such as, for example, various benthic species including plants and other animals having fluorescent properties. As is well known in the art, hybridization stringencies may be adjusted to allow hybridization of nucleic acid probes with complementary sequences of varying degrees of homology. Thus, mcFP polypeptide-encoding nucleic acids may be used to advantage to identify and characterize other genes of varying degrees of relation to mcFP polypeptide, thereby facilitating the discovery of other fluorescent proteins of utility in scientific research.

Nucleic acid molecules, or fragments thereof, encoding mcFP may also be utilized to control the production of a cellular protein, thereby regulating the amount of said protein available to participate in cellular processes. This can be achieved by generating a fluorescently tagged fusion protein comprising mcFP protein linked to a desired polypeptide. Alterations in the physiological amount of said desired polypeptide, in the form of a fluorescently tagged fusion protein, may dramatically affect the activity of said desired polypeptide or other cellular factors that are involved in various cellular processes. Moreover, the presence of the fluorescent tag in such a fusion protein facilitates its visualization within living cells, thereby permitting tracking of said fusion protein over the course of time.

The availability of mcFP polypeptide-encoding nucleic acids enables the production of strains of laboratory mice carrying mcFP-tagged fusion protein genes encoding part or all of a desired polypeptide linked in frame to part or all of the mcFP polypeptide-encoding gene. Such mice may provide an in vivo model for examining function of a desired polypeptide in various cellular processes, including those involved in cell growth and development. The presence of a mcFP fluorescent tag in such a fusion protein facilitates its visualization within living cells, thereby permitting tracking of a fusion protein over the course of time. This feature facilitates studies in which a population of living cells must be analyzed at different temporal windows to evaluate cellular differentiation and potential. In a particular embodiment, a mcFP protein or a mcFP tagged fusion protein could be used as means to track the development of a particular lineage of hematopoietic cells. Since the presence of mcFP protein or a mcFP tagged fusion protein can be detected under conditions which do not adversely affect cell viability, a population of such cells could be returned to the host animal following analysis.

In yet another embodiment of the present invention, the expression of mcFP or a mcFP fusion protein in a cell population may be used as means to track cellular responses to a prophylactic or therapeutic regimen comprised, for example, of treatment with a drug compound.

Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic mice described above will facilitate the molecular elucidation of the role that a desired protein plays in various cellular processes, including: cell proliferation, lineage differentiation, and embryonic development.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration of genetic information may be foreign to the species of animal to which the recipient belongs, or foreign only to the particular individual recipient, or may be genetic information already possessed by the recipient. In the last case, the altered or introduced gene may be expressed differently than the native gene. Such altered or foreign genetic information would encompass the introduction of mcFP or mcFP-tagged fusion proteins derived thereto.

A type of target cell for transgene introduction is the embryonal stem cell (ES). ES cells may be obtained from pre-implantation embryos cultured in vitro (Evans et al., (1981) Nature 292:154–156; Bradley et al., (1984) Nature 309:255–258; Gossler et al., (1986) Proc. Natl. Acad. Sci. 83:9065–9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated mcFP genes as insertional cassettes to selectively inactivate a wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145–147; Bradley et al., (1992) Bio/Technology 10:534–539).

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels $10^5$-fold to $10^2$-fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabinofluranosyl)-5-iodouracil, (FIAU). By this counter selection, the number of homologous recombinants in the surviving transformants can be increased. Utilizing mcFP as a targeted insertional cassette provides means to detect a successful insertion as visualized by acquisition of fluorescence and, therefore, facilitates screening/selection of ES cells with the desired genotype.

As used herein, a "targeted gene" or "knock-out" is a DNA sequence introduced into the germline or a non-human animal by way of human intervention, including but not limited to, the methods described herein. The targeted genes of the invention include DNA sequences which are designed to specifically alter cognate endogenous alleles.

As used herein, the expression of mcFP or a mcFP fusion protein can be targeted in a "tissue specific manner" using a vector in which nucleic acid sequences encoding all or a portion of mcFP are operably linked to regulatory sequences (e.g., promoters and/or enhancers) that direct expression of the encoded fluorescent protein in a particular tissue or cell type.

Methods of use for the transgenic mice of the invention are also provided herein. Transgenic mice into which mcFP or a mcFP fusion protein have been introduced are useful, for example, to identify transgenic animals of a desired genotype, and in studies that require tracking live cells or particular cell populations, including those in which cellular responses to therapeutic agents are being evaluated.

B. mcFP Polypeptides and Antibodies mcFP polypeptides may be used for a variety of purposes in accordance with the present invention. Since fluorescence emission by mcFP does not require tissue fixation, exogenous substrates, and/or cofactors, it is an ideal reporter for studies that require detection of exogenously expressed proteins in living cells and organisms. mcFP can be expressed or introduced into living cells either alone or as a component of a fusion protein. mcFP can be used, for example, in studies designed to monitor gene expression, cell development, or protein localization utilizing protocols to track fluorescent proteins. Such protocols and others, as described above, are well known to those of skill in the art (i.e., Chalfie et al., 1994, Science 263:802–805; Heim et al., 1994, Proc. Nat. Acad. Sci. 91:12501–12504; Chalfie and Prasher, WO 95/07463, Mar. 16, 1995).

It will be apparent to those of skill in the art that mcFP, or a variant or fragment thereof, can be used either alone or in conjunction with other fluorescent protein(s) having distinct excitation/emission spectra for many of the experimental applications envisioned.

Purified mcFP polypeptide, or fragments thereof, may also be used to produce polyclonal or monoclonal antibodies which also may serve as sensitive detection reagents for the presence and accumulation of mcFP-tagged fusion proteins (or complexes containing such fusion proteins) in mammalian cells. Recombinant techniques enable expression of fusion proteins containing part or all of the mcFP polypeptide. The full length proteins or fragments thereof may be used to advantage to generate an array of monoclonal antibodies specific for various epitopes of these proteins, thereby providing additional assays for the detection of mcFP protein or fusion proteins generated therefrom in cells.

Polyclonal or monoclonal antibodies immunologically specific for mcFP polypeptide may be used in a variety of assays designed to detect and quantitate mcFP or fusion proteins generated therefrom. Such assays include, but are not limited to: (1) flow cytometric analysis; (2) immunochemical localization of mcFP-tagged fusion proteins in cells; and (3) immunoblot analysis (e.g., dot blot, Western blot) of extracts from various cells. Additionally, as described above, anti-mcFP polypeptide antibodies can be used for purification of said proteins or fusion proteins generated therefrom (e.g., affinity column purification, immunoprecipitation).

From the foregoing discussion, it can be seen that mcFP polypeptide-encoding nucleic acids, mcFP polypeptide expressing vectors, mcFP polypeptide and anti-mcFP polypeptide antibodies of the invention can be used to detect said mcFP protein gene expression and alter protein accumulation of a desired protein for which a mcFP-tagged fusion protein has been generated for purposes of assessing the role said protein plays in an array of biological processes.

Exemplary approaches for detecting mcFP nucleic acids or polypeptides include: 1) Southern and dot blot analysis; 2) PCR amplification utilizing mcFP specific primers; 3) northern blot analysis; 4) PAGE separation and visualization; 5) Western blot analysis; and 6) utilization of spectrophotometric equipment which provides for illumination of cells, cell lysates, and/or purified proteins at a desired wavelength to facilitate detection of fluorescent proteins which are excited at a particular wavelength of light to emit fluorescence.

The following examples are provided to illustrate certain embodiments of the invention. They are not intended to limit the invention in any way.

EXAMPLE I

Isolation of Full Length mcFP

A novel fluorescent protein mcFP was derived from the coral *Montastrea cavernosa* (*M. cavernosa*). A full length nucleic acid sequence encoding mcFP was determined and is disclosed herein. A full length mcFP nucleic acid sequence comprises 860 base pairs, the open reading frame (726 bp) of which encodes a protein comprised of 225 amino acids. Analysis of the amino acid sequence revealed that mcFP is 73% identical and 84% similar to fluorescent protein FP484 (AF168424, Clavular) and 31% identical and 53% similar with green fluorescent protein (GFP; *Aequorea Victoria*). Of note, the amino acid sequence "QYG" occupies the chromatophore position in mcFP, which differs from that of the "SYG" motif present in GFP. Oligonucleotide probes and/or primers are provided for the amplification of nucleic acids encoding full length mcFP, and fragments and derivatives thereof. Suitable vectors are provided herein for the replication of mcFP nucleic acid sequences and expression of mcFP proteins and derivatives thereof.

Methods and Materials

Sample collection: *M. cavernosa* coral samples were collected at Lee Stocking Island, Caribbean. *M. cavernosa* exhibited orange fluorescence at its base and green fluorescence at its mouth. When the fluorescence is excited at, e.g., 440 nm, three major peaks were recorded for the emission spectra in vivo: ~477 nm (cyan), 510 nm (green, classical GFP) and 578 nm (orange; Gorbunov, M. et al., unpublished data). Coral tissues were collected in 10 mM Tris (pH 8.0) using a water pick and precipitated with 70% ice cold acetone. The samples were centrifuged at 3000 rpm for 10 minutes and air dried into powder.

RNA isolation: 10–30 mg *M. Cavernosa* acetone-treated tissue powder was added to 1 ml pre-chilled TRIzol reagent (Gibco-BRL) and bathed in ice for 20 min. Samples were centrifuged at 12000 g for 10 min. Chloroform (0.25 ml) was added to the supernatant, mixed and centrifuged at 10000 g for 15 min. Re-extraction was performed by sequential addition of acid phenol (pH 4.3, water saturated) and chloroform to the aqueous phase. RNA was precipitated with 0.5 ml ice-cold isopropanol and 0.25 ml sodium acetate (0.8 M, pH 5.5) and sodium chloride (1.2M) for 1.5 hours. The RNA was isolated by centrifugation at 12000 g for 10 min., following which the RNA pellet was washed with 1 ml 70% ethanol. The RNA pellet was air dried and re-solubilized in DEPC treated water.

3' end cDNA amplification: First-strand cDNA synthesis was performed using 0.05–0.1 µg of total RNA using the SMART PCR cDNA Synthesis Kit (Clontech), following the manufacturer's protocol. The protocol was followed to construct a cDNA library, the only methodological deviation involved the use of the TN3 primer (Matz et al., 1999) instead of the CDS cDNA synthesis primer provided in the kit. The double stranded (ds) cDNA was amplified by LD PCR. The PCR primer and TN3 primer were added to a concentration of 0.1 µM in a 50 µl total reaction volume. Thermal cycling was performed as follows: a single cycle of 95° C. for 1 min. and 25 PCR cycles of 95° C., 15 sec.; 65° C., 30 sec.; 68° C., 6 min. using Perkin Elmer GeneAmp PCR System 2400. The 3' RACE PCR was performed as follows: 1 µl of the amplified ds cDNA was added to the master mix, which was comprised of 1× Advantage 2 PCR Polymerase Mix (Clontech), the manufacturer's 1× reaction buffer, 200 µM dNTPs, 0.3 µM of 3' RACE GSP primer and 0.1 µM of the T7-TN3 primer (Matz et al., 1999) in a total volume of 25 µl. The PCR cycles were as follows: a single cycle of 95° C., 10 sec.; 55° C., 1 min.; 72° C., 40 sec.; and 24 cycles of 95° C., 10 secs.; 62° C., 30 sec.; 72° C., 40 sec. The PCR product was diluted 10-fold in water and 1 µl of the dilution mix was added to the nested PCR mix, which included 1× Advantage 2 PCR Polymerase Mix (Clontech), the manufacturer's 1× reaction buffer, 200 µM dNTPs, 0.3 µM of 3' Nested GSP-A primer and 0.1 µM of the TN3 primer in a total volume of 25 µl. Thermal cycling was performed as follows: a single cycle of 95° C., 10 sec.; 55° C., 30 sec.; 72° C., 40 sec.; and 21 cycles of 95° C., 10 sec.; 62° C., 30 sec.; 72° C., 40 sec.

5' end cDNA amplification: cDNA amplification of the 5' end was based on the template-switching effect and step-out PCR (SO-PCR) (Matz et al., 1999). SO-PCR reaction contained 0.5–1 µg of total RNA, 200U of MMLV reverse transcriptase (Superscript II, Gibco), 1× First-Strand Buffer (Clontech), 2 mM DTT (Clontech), 1 mM each of dNTP, 0.5 mM oligo dT and 0.5 mM of template-switching (TS-short) primer (Matz et al., 1999). The reactions proceeded for 90 min at 42° C. One µl of 10-fold diluted first single stand (ss) cDNA was added to a 5' RACE PCR master mix, which contained 1×Advantage2 PCR Polymerase Mix with provided buffer (Clontech), 200 uM dNTPs, 0.15 µM gene-specific primer, 0.02 µM of heel-carrier oligonucleotide and 0.15 µM of heel-specific oligonucleotide (Matz et al., 1999). Thermal cycling was performed by touchdown PCR using 5 cycles of 94° C. for 30 sec.; 72° C., 2.5 min.; 5 cycles of 94° C. for 30 sec.; 70° C. for 2.5 min.; and 25 cycles of 94° C. for 30 sec.; 68° C. for 2.5 min. The heel-carrier oligonucleotide was purified following PAGE separation and the TS-short oligonucleotide was PAGE purified under RNase free conditions.

Cloning and sequencing: Amplified fragments for both 3' and 5' end products were gel purified (ZymoResearch) and cloned into plasmid pCRII using the TA Cloning System (Invitrogen). A 1:1 ratio of vector to insert was used in the ligation reaction, which was performed overnight at 14° C. The resultant ligated product was used to transform TOP 10F' One Shot competent cells (Invitrogen). White colonies, which presumably contain insert in this system, were picked individually and grown in liquid culture to facilitate plasmid isolation and restriction analysis. Recombinant plasmids were isolated using a QIAprep Spin Miniprep Kit and digested by Eco RI (30U for 0.5–1 µg plasmid). 200–400 ng of the recombinant plasmid was used for sequencing. The reaction was performed using the ABI PRISM "Big Dye" Cycle Sequencing Kit. 5.0 pmol of M13 forward and reverse primers (IDTdna) were used to sequence in both directions. The cycle sequence was 96° C. for 30 sec.; and 25 cycles of 96° C. for 10 sec., 50° C. for 5 sec., and 60° C. for 4 min. The reaction product was precipitated by mixing with 1.0 µl of 3M sodium acetate (pH 4.6) and 25 µl 95% ethanol followed by incubation on ice for 10 min. The DNA precipitate was isolated by centrifugation at 4° C. for 30 min. and the resultant pellet was washed with 250 µl of 70% ethanol, air dried, and resuspended in 15 µl of Template Suppressor reagent. The DNA was denatured at 95° C. for 2 min. and loaded on an ABI 310 Sequencing apparatus.

TABLE 1

Primer sequences specific for mcFP

| Primer | Sequence (5'---3') | |
|---|---|---|
| GSP-B7-R1 | GCGTCTTCTTCTGCATAACTGGACC ACTGGAGG | (SEQ ID NO:3) |
| GSP-B7-R2 | AAAGTTCACACCATAAAATCGAATT TCG | (SEQ ID NO:4) |
| B7-Exp-U | ATAGAAGGAGATAGTTAGATGAGTG TGATTAAATCAGTCATGAAA | (SEQ ID NO:5) |
| B7-Exp-D | TCGTTGTCGTTTGGGCTTTTAGTT | (SEQ ID NO:6) |

Results

A full length nucleic acid sequence encoding a novel fluorescent protein, designated mcFP, was isolated from *M. cavernosa* (Eukaryota; Metazoa; Cnidaria; Anthozoa; Zoantharia; Scleractinia; Faviina; Faviidae; Montastraea). A series of primers designed to hybridize to conserved regions of GFP-like proteins and regions specific to the mcFP nucleic acid sequence were used in modified protocols for Rapid Amplification of cDNA at both the 3' and 5' ends (3' RACE and 5' RACE) to amplify the full length mcFP nucleic acid sequence. The mcFP cDNA sequence has 73% amino acid identity with fluorescent protein FP484, 57% with fluorescent protein FP583, and 31% with green fluorescent protein (*Aequorea Victoria*).

The full length nucleic acid sequence of mcFP encodes a protein having a deduced molecular weight of approximately 25,773.43 kilodaltons, a molar extinction coefficient of 27,100, an isoelectric point of 7.84, and a charge of 1.37 at pH 7.

EXAMPLE II

Expression of mcFP

A full length cDNA encoding mcFP was inserted in frame into the pBAD TOPO expression vector. Expressed protein generated using this system can be purified using metal affinity chromatography by virtue of the histidine tag incorporated at the carboxyl terminal end following an in frame fusion. The excitation-emission spectra of mcFP expressed in *E. coli* was measured spectrophotometrically to further characterize the fluorescent properties of the protein. Expression of pure mcFP also facilitates analysis of mcFP crystal structure.

Methods and Materials

Figure 2:
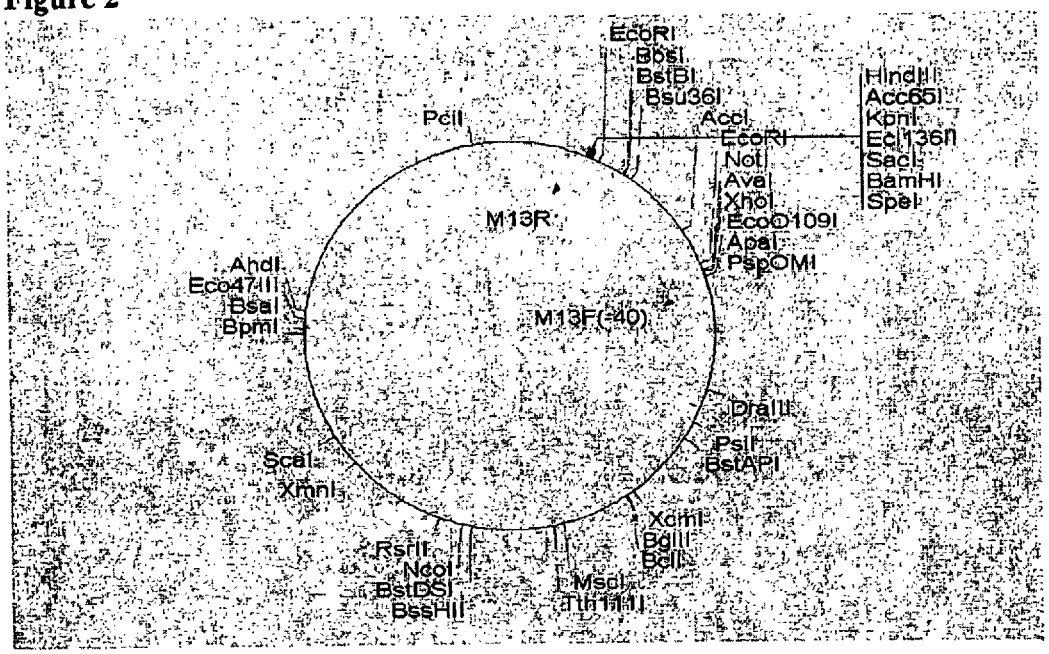
FIG. 2 shows a restriction map of a 5' end of mcFP in the pCRII plasmid (4457 bp)
Figure 3:
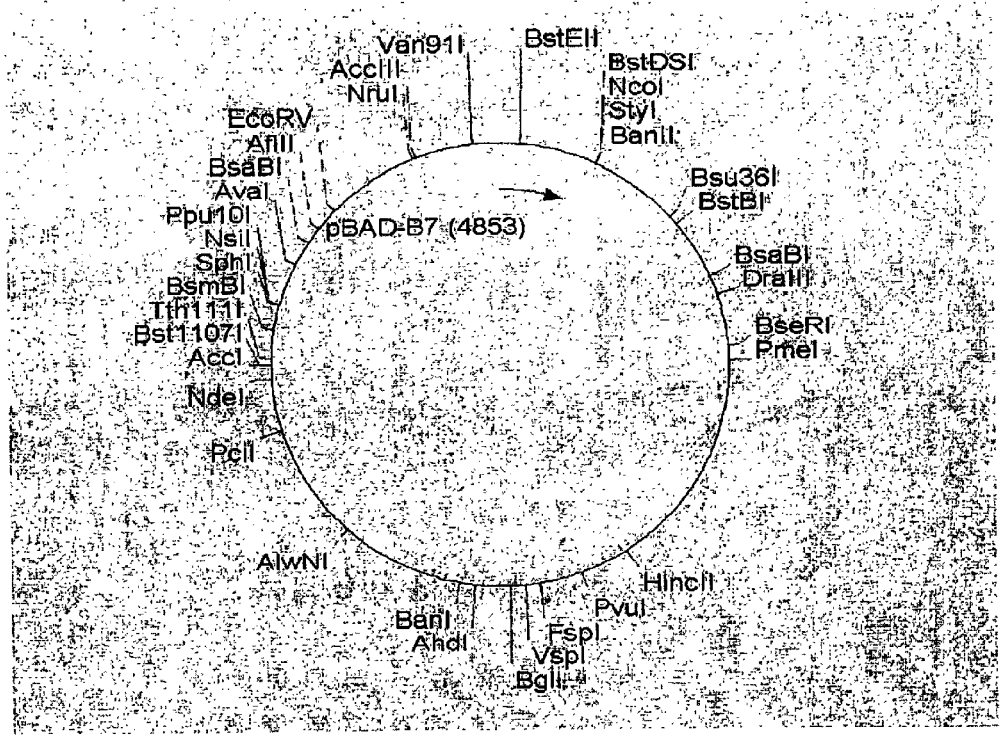
FIG. 3 shows full length mcFP inserted into the expression vector open-pBAD-TOPO (4853 bp circular size)

Ligation and PCR amplification: Recombinant plasmids comprising 3' and 5' end fragments of mcFP (FIGS. 1 and 2) were digested by BstBI and BglII. The restricted fragment from pCRI1-B7-3' end (1179 bp) was ligated to the restricted fragment from pCRII-B7-5' end (3072 bp). Ligation reactions were set up in a total volume of 20 µl comprising 12 µl of double-stranded DNA and 5 µl of T4 DNA ligase (GeneChoice) following the manufacturer's protocol. A pair of primers were designed to amplify the ligated nucleic acid sequences between the 3' and 5' ends of the coding region of the recombinant product. The forward PCR primer (B7-Exp-U; SEQ ID NO: 5) was designed with an in-frame stop codon and a translation reintiation sequence consisting of a ribosome binding site and the first ATG of the protein with a 10 base pair spacer in between. The PCR was performed as follows: 3 µl of ligation product was added to a mixture containing 1× Advantage 2 Polymerase Mix with the manufacturer's buffer (Clontech), 20 μM dNTPs, 0.2 μM of upstream primer (B7-Exp-U; SEQ ID NO: 5) and 0.2 μM of downsteam primer (B7-Exp-D; SEQ ID NO: 6), in a total volume of 20 μl. The cycling profile was as follows: 94° C. for 1 min and then 30 cycles of 94° C. for 30 sec.; 55° C. for 1 min.; 72° C. for 2 min., and 72° C. for 7 min. for the final extension. The amplified fragment was 726 bp in length.

Expression: The PCR product was gel purified (ZymoResearch) and 3' A-overhangs were added post-amplification as follows: the gel purification product was mixed with 0.7 units of Taq polymerase (Titanium), buffer provided by the manufacturer (Clontech), and 1 mM dATP to achieve a total volume of 10 μl, and the mixture was incubated at 72° C. for 10 min. The product was ligated into the pBAD TOPO expression vector (Invitrogen) and then transformed into One Shot Chemically Competent E. coli (Invitrogen). The plasmids were purified from selected colonies using plasmid DNA miniprep kits (Qiagen). Restriction analysis was employed to screen recombinant plasmids to identify those containing the correct insert. The first reaction was performed as follows: 1 μg of plasmid DNA was digested with 20 units of Bam H1 using Buffer E (Promega) in a total volume of 20 μl, at 37° C. for 2 hours. The restriction products were purified by DNA clean & concentrator columns (ZymoResearch) and the purified products were digested in a second restriction by incubation with Bst BI (20 units) in Buffer 4 (New England BioLabs) in a total volume of 20 μl at 65° C. for 2 hours. Three different combinations of restriction digestion products were anticipated to result from the reactions: three fragments of 4403, 334, and 116 kb were predicted to indicate that the insert was positioned in the correct orientation; three fragments of 4283, 454, and 116 kb were predicted to indicate that the insert was positioned in the wrong orientation; and two fragments of 4011 and 116 kb were predicted to indicate the absence of an insert in the plasmid. Recombinant plasmids having the correct orientation, as demonstrated by the pattern of fragments following restriction enzyme digestion, were sequenced using pBAD forward and reverse primers (Invitrogen) according to standard protocols. Nucleotide sequencing confirmed the anticipated mcFP open reading frame and upstream stop codon at position AA270.

Figure 4:
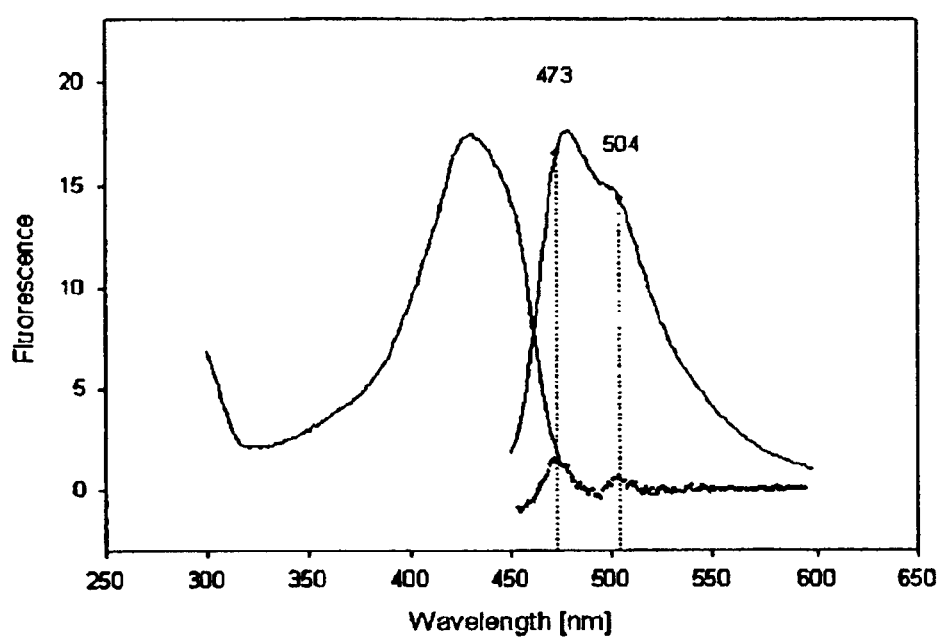
FIG. 4 shows the excitation and emission spectral profiles of novel fluorescent protein mcFP derived from *Montastrea cavernosa*
Figure 5:
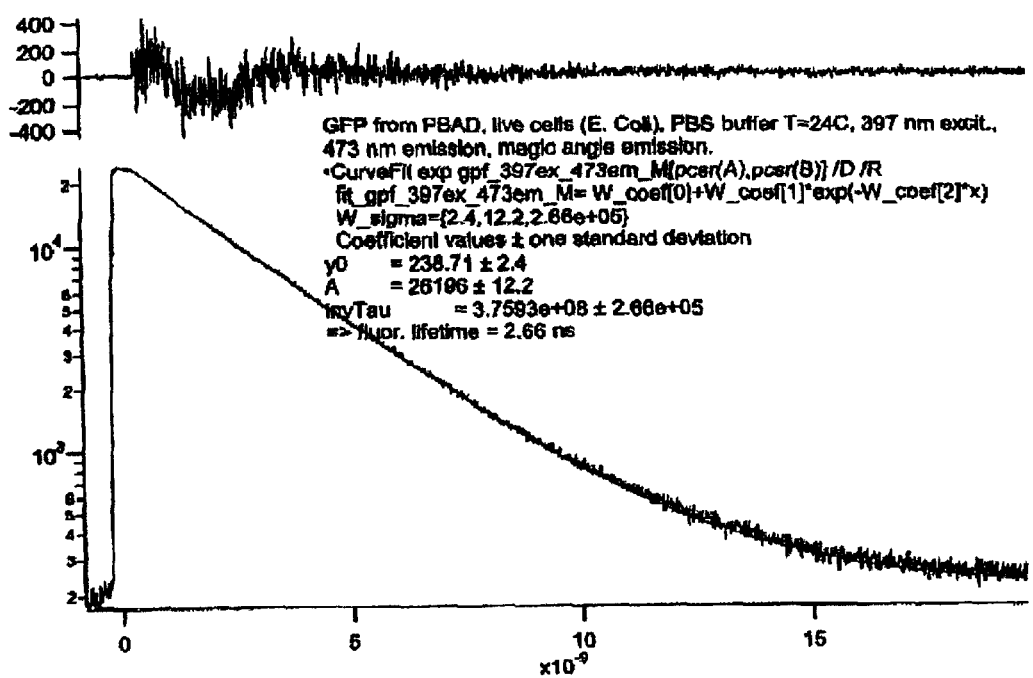
FIG. 5 depicts the fluorescent lifetime of novel fluorescent protein mcFP derived from *Montastrea cavernosa*.

The recombinant clones were grown overnight at 37° C. in 5 ml of LB medium supplemented with 100 μg/ml of ampicillin. 100 μl of the overnight culture was transferred into 10 ml of fresh LB medium containing 100 μg/ml of ampicillin and grown at 37° C. to reach a density of 0.6–0.7 when measured at $OD_{600}$. L-arabinose (0.2%) was added to the culture at this density and the culture was further incubated overnight at 26° C. The cells were pelleted and the cell pellet was resuspended in 1×PBS. The emission and excitation spectrum was measured for the cell suspension comprising recombinant protein mcFP (FIG. 4). The maximum excitation of mcFP was 434 nm and emission was 477 nm. The fluorescent lifetime was 2.66 ns (FIG. 5).

Of note, protein expression in the above system can be regulated by optimizing the L-arabinose concentration over a small range. A time course of expression can also be performed by inducing transformed cultures for 5 to 6 hours, during which time protein isolates can be harvested regularly, to determine if an optimal window for mcFP expression exists. Expressed mcFP may take one day (to a few days) to mature optimally at room temperature. For production of large quantities of mcFP, fluorescent colonies expressing mcFP can be transferred to large volumes of liquid culture to scale-up expression prior to protein purification.

Purification: Expressed mcFP can be purified by binding the 6× His tag that is synthesized at the C-terminus of proteins whose nucleotide sequences are cloned in frame, upstream of the pBAD TOPO transcription stop codon (ProBond Purification System, Invitrogen).

REFERENCES

Matz, M. V., Fradkov, A. F., Labas, Y. A., Savitsky, A. P., Zaraisky, A. G., Markelov, M. L., and Lukyanov, S. A. 1999. Fluorescent proteins from nonbioluminescent Anthozoa species. Nature Biotechnology 17: 969–973.

Matz, M., Shagin, D., Bogdanova, E., Britanov, O., Lukyanov, S., Diatchenko, L., and Chenchik, A. 1999. Amplification of cDNA ends based on template-switching effect and step-out PCR. Nucleic Acids Research 27 (6): 1558–1560.

Fradkov, A. F., Chen, Y., Ding, L., Barsova, E. V., Matz, M. V., Lukyanov, S. A. 2000. Novel fluorescent protein from Discosoma coral and its mutants possesses a unique far-red fluorescence. FEBS Letters 479: 127–130.

A. Terskikh, A. Fradkov, G. Ermakova, A. Zaraisky, P. Tan, A. V. Kajava, A. Zhao, S. Lukyanov, M Matz, S Kim, I. Weissman, P. Siebert. 2000. "Fluorescent Timer": Protein that Changes Color with Time. Science 290: 1585–1588.

S. G. Dove, O. Hoegh-Guldberg, S. Ranganathan. 2001. Major colour patterns of reef-building corals are due to a family of GFP-like proteins. Coral Reefs 19: 197–204.

D. Yarbrough, R. M. Wachter, K. Kallio, M. Matz, and S. J. Remington. 2001 Refined cystal structure of DsREd, a red fluorescent protein from coral, at 2.0-A resolution. PNAS 98(2): 462–467.

G. S. Baird, D. A. Zacharias, and R. Y. Tsien. 2000. Biochemistry, mutagenesis, and oigomerization of DsRed, a red fluorescent protein from coral. PNAS 97 (22): 11984–11989.

A. Salih, A. Larkum, G. Cox, M. Kuhl, and O. Hoegh-Guldberg. 2000. Fluorescent pigments in corals are photoprotective. Nature 408: 850–853.

L. Guzman, D. Belin, M. J. Carson, and J. Beckwith. 1995. Tight Regulation, Modulation, and High-Level Expression by Vectors Containing the Arabinose PBAD Promoter. Journal of Bacteriology 177(14): 4121–4130. Green Fluorescent Protein-Properties, Applications, and Protocols. Edited by M. Chalfie and S. Kain. 1998. A John Wiley & Sons, Inc., Publication.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated nucleic acid molecule comprising SEQ ID NO: 1, said nucleic acid molecule comprising a sequence encoding a *Montastrea cavernosa* fluorescent protein (mcFP) about 225 amino acids in length, said encoded mcFP comprising a polypeptide having fluorescent properties.

2. The nucleic acid molecule of claim 1, which is DNA.

3. The DNA molecule of claim 2, which is a cDNA comprising a sequence approximately 0.86 kilobase pairs in length that encodes said mcFP.

4. The DNA molecule of claim 2, which is a gene comprising introns and exons, the exons of said gene specifically hybridizing with the nucleic acid of SEQ ID NO: 1, and said exons encoding said mcFP, said hybridizing being performed for at least 6 hours at 37–42° C. in a hybridization solution comprising 5×SSC, 5× Denhardt's reagent, 0.5–1.0% SDS, 100 μg/ml denatured salmon sperm DNA, 0.05% sodium pyrophosphate and about 50% formamide.

5. The nucleic acid molecule of claim 1, which is RNA.

6. A vector comprising the nucleic acid molecule of claim 1.

7. A host cell comprising the vector of claim 6.

8. An isolated nucleic acid molecule comprising a sequence selected from the group consisting of:

a) SEQ ID NO: 1;
b) a sequence which specifically hybridizes with SEQ ID NO: 1, said hybridization being performed for at least 6 hours at 37–42° C. in a hybridization solution comprising 5×SSC, 5× Denhardt's reagent, 0.5–1.0% SDS, 100 μg/ml denatured salmon sperm DNA, 0.05% sodium pyrophosphate and about 50% formamide;
c) a sequence encoding a polypeptide of SEQ ID NO: 2; and
d) a nucleic acid sequence encoding a chromophore domain of mcFP.

9. A vector comprising a hybrid nucleic acid molecule, wherein said vector comprises at least one cloning site operably linked to a first nucleic acid sequence molecule of claim 8 and wherein said cloning site provides an insertion site for a second nucleic acid molecule.

10. A host cell comprising the vector of claim 9.

11. A method of identifying a target nucleic acid molecule in a test sample using nucleic acid probe having the sequence shown in SEQ ID NO: 1, the method comprising
a) contacting the probe and the test sample under hybridizing conditions of incubation for at least 6 hours at 37–42° C. in a hybridization solution comprising 5×SSC, 5× Denhardt's reagent, 0.5–1.0% SDS, 100 μg/ml denatured salmon sperm DNA, 0.05% sodium pyrophosphate and about 50% formamide; and
b) observing whether hybridization takes place.

12. The method according to claim 11 wherein the probe is used to identify a mcFP nucleic acid sequence.

* * * * *

SEQUENCE LISTING

<160> NUMBER OF SEQ ID NOS: 6

<210> SEQ ID NO 1
<211> LENGTH: 860
<212> TYPE: DNA
<213> ORGANISM: Montastrea cavernosa

<400> SEQUENCE: 1

```
gtaatacgac tcactatagg gcaagcagtg gtatcaacgc agagtacgcg gggattcacc      60
ctggtgattt ggaagcgagc aaatctagaa gaacaagcgc tgtaagactg atatcttact     120
ttacgtctac catcatgagt gtgattaaat cagtcatgaa aatcaagctg cgtatggacg     180
gcattgtaaa cgggcacaag ttcatgatta caggagaagg tgaaggcaag cctttcgagg     240
gaacacacac tataatactt aaagtcaaag aaggcggacc tctgcctttc gcttacgaca     300
tcttgacaac agcatttcag tacggcaaca gggtattcac caaatacccca aaagacatac    360
cagactattt caagcagtcg tttcctgagg ggtattcctg ggaaagaagc atgactttcg     420
aagaccaggg cgtttgcacc gtcacaagcg acataaagtt ggaaggcgac tgtttttttct    480
acgaaattcg attttatggt gtgaactttc cctccagtgg tccagttatg cagaagaaga    540
cgctgaaatg ggagccatcc actgagaata tgtacgtgcg tgatggagtg ctactggggg    600
atgttagcag gacgctgttg cttgaagggg ataaacatca ccgatgtaac ttcagaagta    660
cttacggggc aaagaagggt gtcgtgttgc agaatatca ctttgtggac caccgaattg     720
aaattctgag ccatgacaaa gattacaaca ccgttgaggt gtatgagaat gccgttgctc    780
gcccttctat gctgccggtt aaggccaagt aaaggcttaa ctaaaagccc aaacgacaac    840
gaggagaaaa aaaaaaaaaa                                                860
```

<210> SEQ ID NO 2
<211> LENGTH: 225
<212> TYPE: PRT
<213> ORGANISM: Montastrea cavernosa

<400> SEQUENCE: 2

```
Met Ser Val Ile Lys Ser Val Met Lys Ile Lys Leu Arg Met Asp Gly
1               5                   10                  15

Ile Val Asn Gly His Lys Phe Met Ile Thr Gly Glu Gly Glu Gly Lys
            20                  25                  30

Pro Phe Glu Gly Thr His Thr Ile Ile Leu Lys Val Lys Glu Gly Gly
        35                  40                  45

Pro Leu Pro Phe Ala Tyr Asp Ile Leu Thr Thr Ala Phe Gln Tyr Gly
    50                  55                  60

Asn Arg Val Phe Thr Lys Tyr Pro Lys Asp Ile Pro Asp Tyr Phe Lys
65                  70                  75                  80

Gln Ser Phe Pro Glu Gly Tyr Ser Trp Glu Arg Ser Met Thr Phe Glu
                85                  90                  95

Asp Gln Gly Val Cys Thr Val Thr Ser Asp Ile Lys Leu Glu Gly Asp
            100                 105                 110

Cys Phe Phe Tyr Glu Ile Arg Phe Tyr Gly Val Asn Phe Pro Ser Ser
        115                 120                 125

Gly Pro Val Met Gln Lys Lys Thr Leu Lys Trp Glu Pro Ser Thr Glu
    130                 135                 140

Asn Met Tyr Val Arg Asp Gly Val Leu Leu Gly Asp Val Ser Arg Thr
145                 150                 155                 160
```

```
Leu Leu Leu Glu Gly Asp Lys His His Arg Cys Asn Phe Arg Ser Thr
            165                 170                 175

Tyr Gly Ala Lys Lys Gly Val Val Leu Pro Glu Tyr His Phe Val Asp
            180                 185                 190

His Arg Ile Glu Ile Leu Ser His Asp Lys Asp Tyr Asn Thr Val Glu
            195                 200                 205

Val Tyr Glu Asn Ala Val Ala Arg Pro Ser Met Leu Pro Val Lys Ala
        210                 215                 220

Lys
225

<210> SEQ ID NO 3
<211> LENGTH: 33
<212> TYPE: DNA
<213> ORGANISM: Artificial Sequence
<220> FEATURE:
<223> OTHER INFORMATION: primer

<400> SEQUENCE: 3
gcgtcttctt ctgcataact ggaccactgg agg                                      33

<210> SEQ ID NO 4
<211> LENGTH: 28
<212> TYPE: DNA
<213> ORGANISM: Artificial Sequence
<220> FEATURE:
<223> OTHER INFORMATION: primer

<400> SEQUENCE: 4
aaagttcaca ccataaaatc gaatttcg                                            28

<210> SEQ ID NO 5
<211> LENGTH: 45
<212> TYPE: DNA
<213> ORGANISM: Artificial Sequence
<220> FEATURE:
<223> OTHER INFORMATION: primer

<400> SEQUENCE: 5
atagaaggag atagttagat gagtgtgatt aaatcagtca tgaaa                         45

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
tcgttgtcgt ttgggctttt agtt                                                24
```